United States Patent [19]

Odanaka et al.

[11] 4,283,580
[45] Aug. 11, 1981

[54] PROCESS FOR THE PRODUCTION OF ALKYLENE GLYCOLS

[75] Inventors: Hiroshi Odanaka, Yokosuka; Minoru Saotome; Toshihiko Kumazawa, both of Yokohama, all of Japan

[73] Assignee: Nippon Shokubai Kagaku Kogyo Co., Ltd., Osaka, Japan

[21] Appl. No.: 76,843

[22] Filed: Sep. 19, 1979

[30] Foreign Application Priority Data

May 24, 1979 [JP] Japan .................................. 54-63259
May 24, 1979 [JP] Japan .................................. 54-63260

[51] Int. Cl.$^3$ ....................... C07C 31/30; C07C 33/26
[52] U.S. Cl. .................................. 568/858; 568/700; 568/811; 568/857
[58] Field of Search ................ 568/858, 811, 700, 857

[56] References Cited

U.S. PATENT DOCUMENTS 2,807,651  9/1957  Britton et al. ......................... 568/867
3,629,343  12/1971  Levin et al. ........................... 568/867

FOREIGN PATENT DOCUMENTS 267618  7/1970  U.S.S.R. .................................. 568/858

OTHER PUBLICATIONS

Peppel, "Ind. to Eng. Chem.", vol. 50, No. 5, May 1958, pp. 767–770.

*Primary Examiner*—Joseph E. Evans
*Attorney, Agent, or Firm*—Omri M. Behr

[57] ABSTRACT

A process for the production of alkylene glycols, which comprises causing a corresponding alkylene carbonate to react with water in the presence of a catalyst of at least one member selected from the group consisting of molybdenum and tungsten.

15 Claims, No Drawings

PROCESS FOR THE PRODUCTION OF ALKYLENE GLYCOLS

This invention relates to a process for the production of alkylene glycols, and more particularly it relates to a process for producing alkylene glycols involving a high percentage yield of a monoalkylene glycol by causing a corresponding alkylene carbonate to react with water in the presence of a catalyst of at least one member selected from the group consisting of molybdenum and tungsten.

Alkylene glycols such as ethylene glycol and propylene glycol have heretofore been extensively used as raw materials for polyesters, polyethers, antifreezes, surfactants, etc.

Heretofore for the manufacture of alkylene glycols by the reaction of the corresponding alkylene oxides with water, a method which effects the reaction by use of a catalyst such as of sulfuric acid (U.S. Pat. No. 2,255,411) and a method which carries out the reaction at an elevated temperature and increased pressure without use of any catalyst have been adopted on commercial scales. In addition to forming monoalkylene glycols, however, these methods inevitably by-produce large amounts of dialkylene glycols, trialkylene glycols, tetraalkylene glycols and other polyalkylene glycols. Generally in the uses which are found for alkylene glycols, those for dialkylene glycols, trialkylene glycols, tetraalkylene glycols and other polyalkylene glycols are few compared with those for monoalkylene glycols. In the production of alkylene glycols by the reaction of alkylene oxides with water, therefore, need is felt for the desirability of the development of a method which is capable of producing alkylene glycols having monoalkylene glycols formed therein in high percentages.

The proportions in which the various alkylene glycols are formed by the reaction of a corresponding alkylene oxide with water depend on the molar ratio of water to the alkylene oxide. To increase the proportion of monoalkylene glycol in the total composition of alkylene glycols formed by the reaction, it is necessary to increase the molar ratio of water to the alkylene oxide. Generally, the conversion of an alkylene oxide to corresponding alkylene glycols is effected by bringing to completion the reaction of the alkylene oxide with such a large excess of water as to give a water:alkylene oxide molar ratio in the range of from 10:1 to 20:1 under the conditions of 5 to 25 kg/cm$^2$G. of pressure and 100° to 200° C. of temperature in the presence or absence of a catalyst. The production which is obtained by the reaction of the alkylene oxide with the large excess of water, however, is a dilute aqueous solution containing alkylene glycols in a low concentration of from 5 to 30% by weight. To separate the alkylene glycols in a refined form from this dilute aqueous solution, removal of the large excess of water is inevitably entailed. This method, therefore, has the disadvantage that the removal of such excess water necessitate installation of a complicate apparatus such as an evaporator and consumption of a huge volume of energy.

Another method for producing alkylene glycols resorts, as disclosed in U.S. Pat. No. 4,117,250, for example, to a procedure which comprises causing a corresponding alkylene carbonate to react with water of an amount slightly in excess of the stoichiometric amount under the condition of 120°-200° C. of temperature in the presence of a carbonate of an alkali metal such as potassium carbonate. In the reaction using such a catalyst as mentioned above, however, the reaction velocity is so low that the reaction temperature must be elevated to expedite the reaction by reason of economy of operation. The elevation of the reaction temperature has a possibility of the heat adversely affecting the quality of the alkylene glycol which is obtained by refining the reaction solution. When this reaction is carried out under mild conditions, there ensues a disadvantage that unaltered alkylene carbonate combines with the reaction product to form an azeotrope which renders the isolation of the produced alkylene glycol difficult.

It is, therefore, an object of this invention to provide a process which permits the production of monoalkylene glycol in a high yield and represses the possible by-production of polyalkylene glycols by causing a corresponding alkylene carbonate to react with water.

Another object of this invention is to provide a process for the production of alkylene glycol, which enables the amount of water used for reaction with a corresponding alkylene carbonate to be decreased substantially to the neighborhood of the stoichiometric amount and, therefore, permit a reduction in the energy consumed in the subsequent step for the refining of the formed alkylene glycol.

These objects have now been accomplished by the process of this invention which produces alkylene glycols by causing a corresponding alkylene carbonate to react with water in the presence of a catalyst of at least one member selected from the group consisting of molybdenum and tungsten.

The alkylene carbonates to which the process of the present invention can be effectively applied are chiefly the compounds of the general formula I:

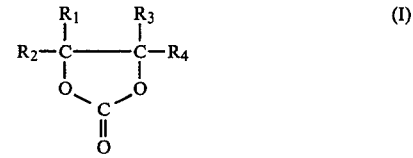

wherein, $R_1$, $R_2$, $R_3$ and $R_4$ each denote a hydrogen atom, an alkyl group having 1 to 3 carbon atoms, an aryl group having 6 carbon atoms, an alkenyl group having 2 or 3 carbon atoms or a cycloalkyl group having 3 to 6 carbon atoms. Typical of these compounds are ethylene carbonate and propylene carbonate.

The reaction by the process of this invention produces, from alkylene carbonates described above, corresponding alkylene glycols represented by the general formula II:

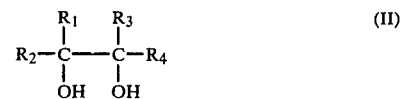

wherein, $R_1$, $R_2$, $R_3$ and $R_4$ represent the same substituents as those of the aforementioned general formula I. Typical of these compounds are ethyleen glycol and 1,2-propylene glycol.

Water of any type can be effectively used as the raw material for the reaction of this invention. Particularly, fresh water, the water obtained by an ion-exchange treatment, the condensate of steam or the condensate issuing from the step of dehydration in the plant for the production of alkylene oxide or alkylene glycol may be advantageously used. In the reaction of this invention, the amount of water to be used for the reaction with an alkylene carbonate can be decreased to the stoichiometric amount. Depending on the type of reaction, the amount of water may be further decreased. From the practical point of view, it is desirable to use water in an amount slightly in excess of the stoichiometric amount, namely 1.01 to 5 times the molar equivalent, most preferably 1.01 to 2.5 times the molar equivalent. The amount of water, however, is not necessarily critical.

As the catalyst for the process of this invention, molybdenum or tungsten is used in the form of pure metal or a compound. In the case of metallic molybdenum, it is desired to have a large surface area. For actual use as the catalyst, it may be prepared in the form of powder, grains like those of sand, granules, a metal gauze, a honeycomb or a sponge and, in that form, mixed, suspended or deposited as a fixed bed in the liquid phase of the reactants. Otherwise, the material of which the reactor is made may contain metallic molybdenum to serve as the catalyst. From the various forms described above, a suitable form may be selected in due consideration of such factors as the reactivity, ease of handling and cost. It is particularly desirable to use metallic molybdenum of a form which can be dispersed into very fine particles in the reaction system.

Molybdenum compounds which are suitable for use as the catalyst in the reaction include both inorganic and organic compounds such as, for example, oxides, sulfides, acids, halides, phosphorus compounds, poly acids, alkali metal salts of such acids and poly acids, alkaline earth metal salts of such acids and poly acids, ammonium salts of sch acids and poly acids, heavy metal salts of acids and organic acid salts. Typical of these compounds are molybdenum dioxide, molybdenum trioxide, molybdenum disulfide, molybdic acid, molybdenum trichloride, molybdenum pentachloride, molybdenum tribromide, phosphomolybdic acid, ammonium phosphomolybdate, sodium molybdate, sodium paramolybdate, potassium molybdate, potassium paramolybdate, lithium molybdate, calcium molybdate, barium molybdate, ammonium molybdate, ammonium paramolybdate, iron molybdate and lead molybdate.

The metallic molybdenum and any of the molybdenum compounds described above may be used in the form of a mixture. Of the various molybdenum compounds which are usable as the catalyst for the reaction, particularly desirable are molybdic acid and salts thereof, especially alkali metal salts of molybdic acid such as sodium molybdate and potassium molybdate.

Where metallic tungsten is selected for use as the catalyst, it is desired to have a large surface area. For actual use, the metallic tungsten may be prepared in the form of powder, grains like those of sand, granules, a metal gauze, a honeycomb or a sponge and, in that form, mixed, suspended or deposited as a fixed bed in the liquid phase of the reactants. Otherwise, the material of which the reactor is made may contain metallic tungsten to serve as the catalyst. Of the various forms described above, a suitable form may be selected in due consideration of such factors as the reactivity, ease of handling and cost. It is particularly desirable to use metallic tungsten of a form which can be dispersed into very fine particles in the reaction system.

Tungsten compounds which are suitable for use as the catalyst in the reaction include both inorganic and organic compounds such as, for example, oxides, acids, halides, phosphorus compounds, poly acids, alkali metal as salts of such acids and poly acids, alkaline earth metal salts of such acids and poly acids, ammonium salts of such acids and poly acids, heavy metal salts of acids and organic acids salts. Typical of these compounds are tungsten dioxide, tungsten trioxide, tungstic acid, tungsten dichloride, tungsten pentachloride, tungsten dibromide, tungsten pentabromide, phosphotungstic acid, potassium tungstate, sodium tungstate, lithium tungstate, potassium paratungstate, sodium paratungstate, sodium metatungstate, calcium tungstate, barium tungstate, magnesium tungstate, ammonium tungstate, ammonium paratungstate, cadmium tungstate, cobalt tungstate, ferric tungstate, lead tungstate, cupric tungstate and bismuth tungstate.

The metallic tungsten and any of the tungsten compounds described above may be used in the form of a mixture. Of the various tungsten compounds which are usable as the catalyst for the reaction, particularly desirable are tungstic acid and salts thereof, especially alkali metal salts of tungstic acid such as sodium tungstate and potassium tungstate.

The catalyst of at least one member selected from the group consisting of molybdenum and tungsten according to the present invention is used in an amount of not less than 0.01 mol% based on the alkylene carbonate. The effect of of the catalyst increases with the amount in which the catalyst is used. When the amount of the catalyst exceeds 0.5 mol%, the reaction starts even at normal room temperature and normal pressure and proceeds with liberation of a large amount of carbon dioxide. In the reaction performed on a commercial scale, however, the amount of the catalyst to be added to the reactants is limited automatically. Generally, it is suitable selected in the range of from 0.05 to 10 mol%.

The catalyst of this invention is used in its unmodified form or in a form molded or supported by a known method on a carrier such as of silica, alumina or zeolite. The catalyst of such a form is dissolved, mixed or suspended or deposited as a fixed bed in the liquid phase of the reactants. The addition of the catalyst to the reactants is accomplished by mixing the catalyst with the water used for the reaction or by means of an inlet installed separately in the equipment for the reaction. In any event, the catalyst is added in its whole amount all at once to the reactants at the start of the reaction or it is added continuously or intermittently at a fixed feed rate throughout the entire reaction time. A suitable method of addition may be selected in due consideration of such factors as the type of reaction and the manner of operation.

The reaction temperature, though variable with such factors as the type of alkylene carbonate used as the raw material, the type of the catalyst and the initial composition of the reactant solution, is generally in the range of from 20° to 180° C., preferably from 50° to 170° C. Although the reaction pressure is limited to the range of from 0 to 50 kg/cm$^2$G, preferably from 0 to 30 kg/cm$^2$G so as to retain the reactants in a liquid phase, the reaction may be carried out under a reduced pressure where there is used a condenser capable of preventing otherwise possible loss of water. As occasion demands, the pressure inside the reactor may be suitably adjusted. The reaction according to the present invention can be effectively performed batchwise, semibatchwise or continuously.

Now, the process of the present invention will be specifically described below by reference to working examples, which are cited solely for the purpose of illustration and are not meant to limit the present invention in any sense. Needless to mention, they admit of various modifications thereto without departing from the spirit of this invention.

EXAMPLE 1

A stainless steel autoclave having an inner volume of 200 ml and equipped with a stirrer was charged with 66.0 g of ethylene carbonate, 14.9 g of water and 0.39 mol% based on the ethylene carbonate of potassium molybdenum as the catalyst. The autoclave was submerged in an oil bath kept at 150° C. and left to stand therein for 90 minutes to allow the contents to react. In the first 9 minutes of the standing, the inner pressure of the autoclave rose from 0 kg/cm²G to 15 kg cm²G. Thereafter, the reaction was carried out with continued removal of the $CO_2$ gas liberated by the reaction, with the inner pressure of the autoclave controlled in the range of from 10 to 15 kg/cm²G. On completion of the reaction, the autoclave was immediately cooled in an ice bath and the contents were analyzed. Consequently, the conversion of the ethylene carbonate was found to be 100% and the selectivity to monoethylene glycol to be 100%, while no diethylene glycol was detected.

CONTROL 1

A stainless steel autoclave similar to the autoclave of EXAMPLE 1 was charged with 66.0 g of ethylene carbonate, 14.9 g of water and 0.39 mol% based on the ethylene carbonate of potassium bicarbonate as the catalyst. The autoclave was then left to stand for 90 minutes under the same conditions as those of EXAMPLE 1 to allow the contents to react. In the course of the reaction, it took 20 minutes for the inner pressure of the autoclave to reach 15 kg/cm²G. On completion of the reaction, the contents of the autoclave were analyzed by gas chromatography. Consequently, the conversion of ethylene carbonate was found to be 99.2 mol%, the selectivity to monoethylene glycol to be 99.9 mol% and the concentration of the byproduced diethylene glycol to be 0.1 mol%.

EXAMPLE 2

A glass flask having an inner volume of 200 ml was charged with 44.0 g of ethylene carbonate, 18.0 g of water and 0.5 mol% based on the ethylene carbonate of sodium molybdate as the catalyst. The glass flask, with a watercooled condenser attached to the upper portion thereof, was submerged in an oil bath kept at 90° C. and left to stand therein at normal pressure for 120 minutes. The results of the reaction were as shown in Table 1.

EXAMPLES 3-4

The procedure of EXAMPLE 2 was repeated, except that the catalyst and reaction conditions were charged as indicated in Table 1. The results of the reaction were as shown in Table 1.

CONTROLS 2-5

The procedure of EXAMPLE 2 was repeated, except that the catalyst and reaction conditions were changed as indicated in Table 1. The results of the reaction were as shown in Table 1.

CONTROL 6

The procedure of EXAMPLE 2 was repeated, except that the use of the catalyst was omitted. The result of the reaction were as shown in Table 1.

TABLE 1

| | Catalyst | | Reaction conditions | | Results |
|---|---|---|---|---|---|
| Example | Kind | Amount to ethylene carbonate (mol %) | Temp. (°C.) | Time (min.) | Conversion of ethylene carbonate (mol %) |
| 1 | Potassium molybdate | 0.39 | 150 | 90 | 100 |
| 2 | Sodium molybdate | 0.5 | 90 | 120 | 64.6 |
| 3 | Potassium molybdate | 0.5 | 90 | 120 | 67.9 |
| 4 | Potassium molybdate | 0.5 | 105–115 | 90 | 99.9< |
| Control | | | | | |
| 1 | Potassium bicarbonate | 0.39 | 150 | 90 | 99.2 |
| 2 | Potassium bicarbonate | 0.5 | 90 | 120 | 16.6 |
| 3 | Potassium bicarbonate | 0.5 | 90 | 120 | 18.4 |
| 4 | Potassium carbonate | 0.5 | 90 | 120 | 21.4 |
| 5 | Sodium carbonate | 0.5 | 90 | 120 | 15.9 |
| 6 | None | 0 | 90 | 120 | 9.1 |

EXAMPLE 5-6

The same reactor vessel as used in Example 2 was charged with 51.0 g of propylene carbonate, 18.0 g of water and 0.5 mol% based on the propylene carbonate of a varying catalyst shown in Table 2. The reactor was left to stand at 120° C. for 120 minutes to allow the contents to react. The results of the reaction were as shown in Table 2.

CONTROL 7

The same reactor vessel as used in EXAMPLE 2 was charged with 51.0 g of propylene carbonate, 18.0 g of water and 0.5 mol% based on the propylene carbonate of potassium carbonate as the catalyst. The reactor was left to stand under the same conditions as those of EXAMPLES 5-6 to allow the contents to react. The results of the reaction were as shown in Table 2.

TABLE 2

| | Catalyst | | Reaction conditions | | Results |
|---|---|---|---|---|---|
| Example | Kind | Amount of propylene carbonate (mol %) | Temp. (°C.) | Time (min.) | Conversion of propylene carbonate (mol %) |
| 5 | Potassium molybdate | 0.5 | 110 | 120 | 54.8 |
| 6 | Sodium molybdate | 0.5 | 110 | 120 | 50.5 |
| 7 | Potassium carbonate | 0.5 | 110 | 120 | 15.9 |

EXAMPLE 8

The procedure of EXAMPLE 1 was repeated, except that 0.39 mol% based on the ethylene carbonate of potassium tungstate was used as the catalyst in the place of potassium molybdate. On analysis of the reaction, the conversion of ethylene carbonate was found to be 100% and the selectivity to monoethylene glycol to be 100% and no by-product of diethylene glycol was detected.

EXAMPLE 9

A glass flask having an inner volume of 200 ml was charged with 44.0 g of ethylene carbonate, 18.0 g of water and 0.5 mol% based on the ethylene carbonate of potassium tungstate as the catalyst. The flask, with a water-cooled condenser attached to the upper portion thereof, was submerged in an oil bath kept at 90° C. and left to stand at normal pressure for 120 minutes to allow the contents to react. The results of the reaction were as shown in Table 3.

EXAMPLES 10-11

The procedure of EXAMPLE 9 was repeated, except that the catalysts and the reaction conditions indicated in Table 3 were used. The results of the reaction were as shown in Table 3.

TABLE 3

| | Catalyst | | Reaction Conditions | | Results |
|---|---|---|---|---|---|
| | | Amount to ethylene | | | Conversion of ethylene |
| Example | Kind | carbonate (mol %) | Temp. (°C.) | Time (min) | carbonate (mol %) |
| 8 | Potassium tungstate | 0.39 | 150 | 90 | 100 |
| 9 | Potassium tungstate | 0.5 | 90 | 120 | 29.9 |
| 10 | Sodium tungstate | 0.5 | 90 | 120 | 25.1 |
| 11 | Potassium tungstate | 0.5 | 105-115 | 90 | 90 |

EXAMPLE 12-13

The same reaction vessel as used in EXAMPLE 9 was charged with 51.0 g of propylene carbonate, 18.0 g of water and 0.5 mol% based on the propylene carbonate of a varying catalyst indicated in Table 4. The reactor was left to stand at a reaction temperature of 90° C. for 120 minutes to allow the contents to react. The results of the reaction were as shown in Table 4.

CONTROL 8

The procedure of EXAMPLE 9 was repeated, except that propylene carbonate was used in place of ethylene carbonate and the use of the catalyst was omitted. The results of the reaction were as shown in Table 4.

TABLE 4

| | Catalyst | | Reaction condition | | Results |
|---|---|---|---|---|---|
| | | Amount to propylene | | | Conversion of |
| Example | Kind | carbonate (mol %) | Temp. (°C.) | Time (min) | propylene carbonate (mol %) |
| 12 | Potassium tungstate | 0.5 | 90 | 120 | 10.5 |
| 13 | Sodium tungstate | 0.5 | 90 | 120 | 10.1 |
| Control 8 | None | 0 | 90 | 120 | 2.7 |

What is claimed is:

1. A process for the production of substituted or unsubstituted ethylene glycols, which comprises causing a corresponding substituted or unsubstituted ethylene carbonate of the formula $$R_2-\underset{\underset{O}{|}}{\overset{\overset{R_1}{|}}{C}}-\underset{\underset{O}{|}}{\overset{\overset{R_3}{|}}{O}}-R_4$$
$$\underset{O}{\overset{C}{\diagdown\diagup}}$$

wherein, $R_1$, $R_2$, $R_3$ and $R_4$ each denote a hydrogen atom, an alkyl group having 1 to 3 carbon atoms, an aryl group having 6 carbon atoms, an alkenyl group having 2 or 3 carbon atoms or a cycloalkyl group having 3 to 6 carbon atoms, to react with water in the presence of a catalyst of at least one member selected from the group consisting of molybdenum and tungsten in metal or compound form.

2. A process according to claim 1, wherein the amount of the catalyst is not less than 0.01 mol% based on the ethylene carbonate.

3. A process according to claim 2, wherein the amount of the catalyst is from 0.05 to 10 mol% based on the ethylene carbonate.

4. A process according to claim 1, wherein the reaction is carried out at a temperature in the range of from 20° to 180° C.

5. A process according to claim 1, wherein the ethylene carbonate is ethylene carbonate or propylene carbonate.

6. A process according to claim 1, wherein the catalyst is metallic molybdenum.

7. A process according to claim 1, wherein the catalyst is a molybdenum compound.

8. A process according to claim 7, wherein the molybdenum compound is molybdic acid or a salt thereof.

9. A process according to claim 8, wherein the salt of molybdic acid is an alkali metal salt.

10. A process according to claim 1, wherein the catalyst is metallic tungsten.

11. A process according to claim 1, wherein the catalyst is a tungsten compound.

12. A process according to claim 11, wherein the tungsten compound is tungstic acid or a salt thereof.

13. A process according to claim 12, wherein the salt of tungstic acid is an alkali metal salt.

14. A process according to claim 1, wherein the amount of water is 1.01 to 5 mols per mol of the ethylene carbonate.

15. A process according to claim 14, wherein the amount of water is 1.01 to 2.5 mols per mol of the ethylene carbonate.

* * * * *